United States Patent [19]
Smith et al.

[11] Patent Number: 5,360,211
[45] Date of Patent: Nov. 1, 1994

[54] SPRINGS AND LOCKING COLLARS FOR RETRACTABLE SLEEVE-PROTECTED INJECTION APPARATUS

[75] Inventors: Craig W. Smith; Randall E. Ohnemus, both of Ventura, Calif.

[73] Assignee: InjectiMed, Inc., Ventura, Calif.

[21] Appl. No.: 110,889

[22] Filed: Aug. 24, 1993

Related U.S. Application Data

[62] Division of Ser. No. 850,442, Mar. 10, 1992, Pat. No. 5,261,894.

[51] Int. Cl.⁵ .............................................. F16F 1/06
[52] U.S. Cl. ..................................... 267/180; 267/169
[58] Field of Search ............... 267/166, 169, 180, 182, 267/287, 152, 33; 264/281, DIG. 40

[56] References Cited

U.S. PATENT DOCUMENTS

| | | | |
|---|---|---|---|
| 1,432,604 | 10/1922 | Lang | 267/169 X |
| 2,033,035 | 3/1936 | Koons | 267/169 X |
| 2,118,150 | 5/1938 | Brinkley | 267/169 X |
| 3,340,965 | 9/1967 | Ellis, Jr. | 188/287 |
| 4,869,471 | 9/1989 | Schwarz et al. | 267/180 X |

Primary Examiner—Robert J. Oberleitner
Assistant Examiner—Lee W. Young
Attorney, Agent, or Firm—Donald A. Streck

[57] ABSTRACT

This is an all-plastic protective sleeve for the needle of a medical device. It comprises, a plastic base carrying a bottom end of the needle; a plastic end-cap slidably mounted on the needle adjacent a tip end thereof; a plurality of longitudinal plastic slats extending from the base to the end-cap; a cylindrical plastic locking collar disposed over the plurality of longitudinal slats adjacent the end-cap; and, a plastic spring disposed over the plurality of longitudinal slats between the base and the end-cap. The spring is a unitary plastic helical compression spring comprising a cylindrical collar portion disposed over a center portion of the plurality of longitudinal slats with first and second portions of helical compression spring turns extending therefrom toward the base and the locking collar, respectively. The locking collar has an outside diameter larger than the outside diameter of the spring and is of a thickness sufficient to produce a textured grippable area at the periphery thereof.

2 Claims, 3 Drawing Sheets

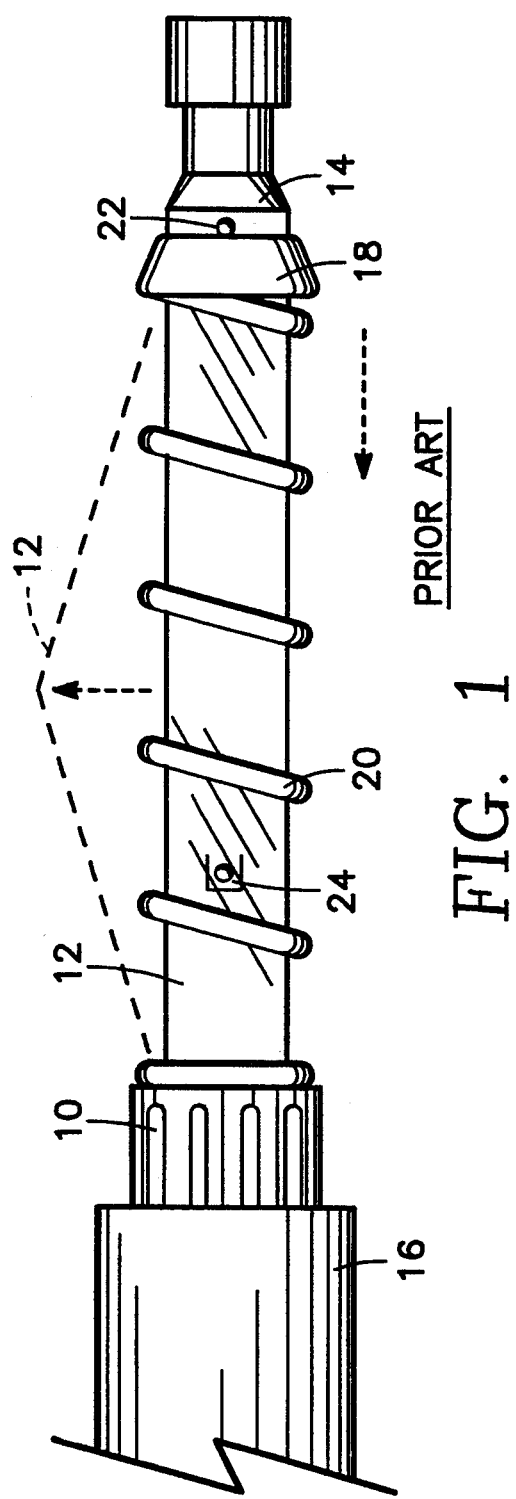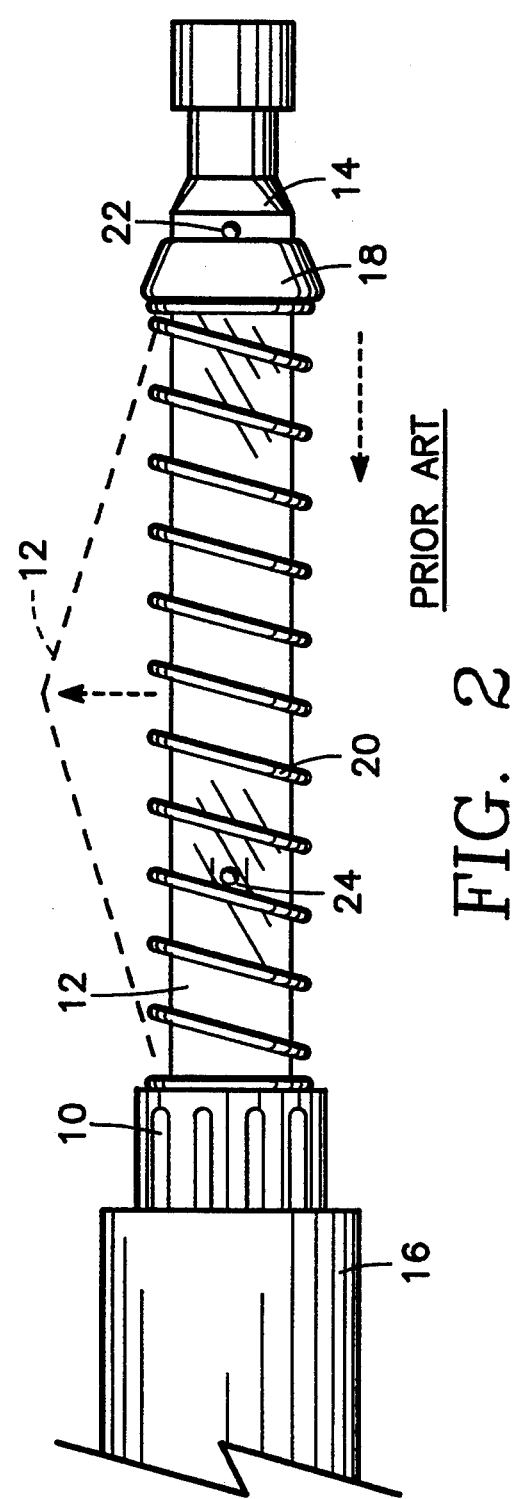

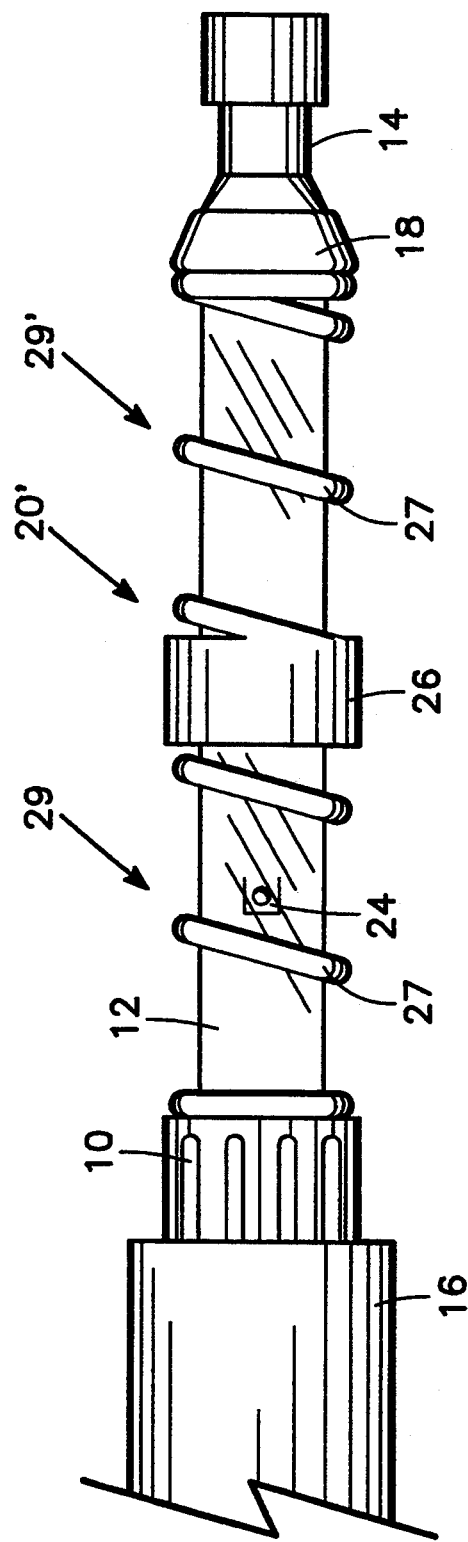
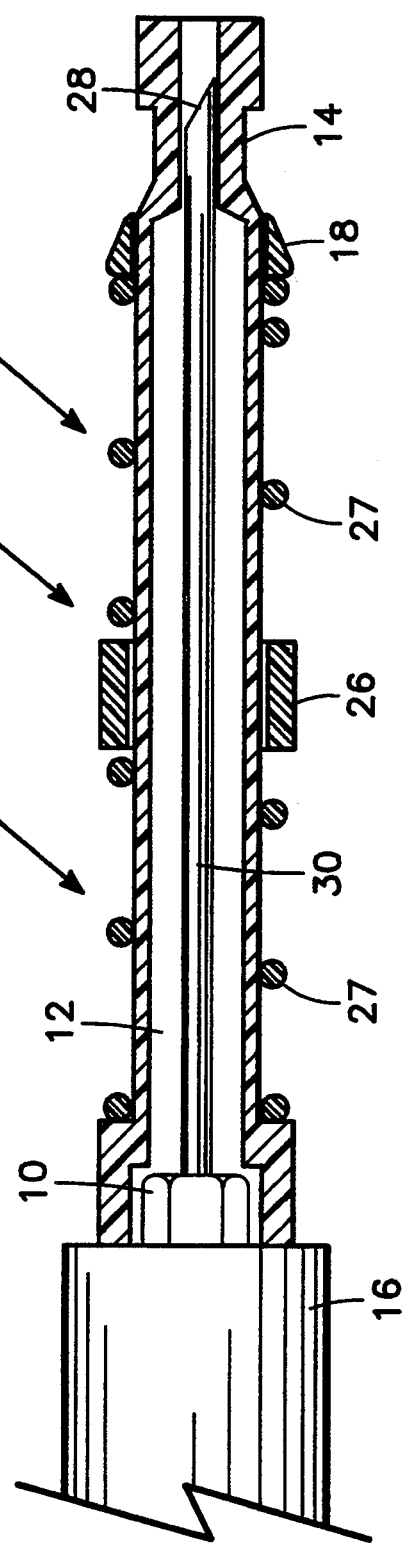

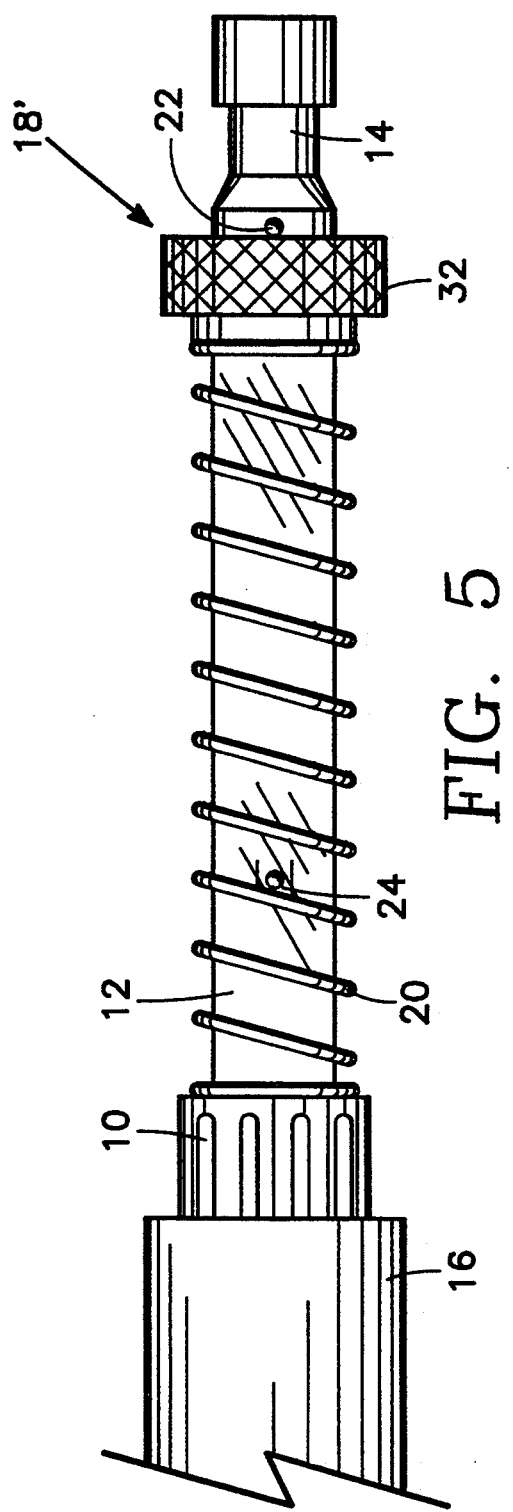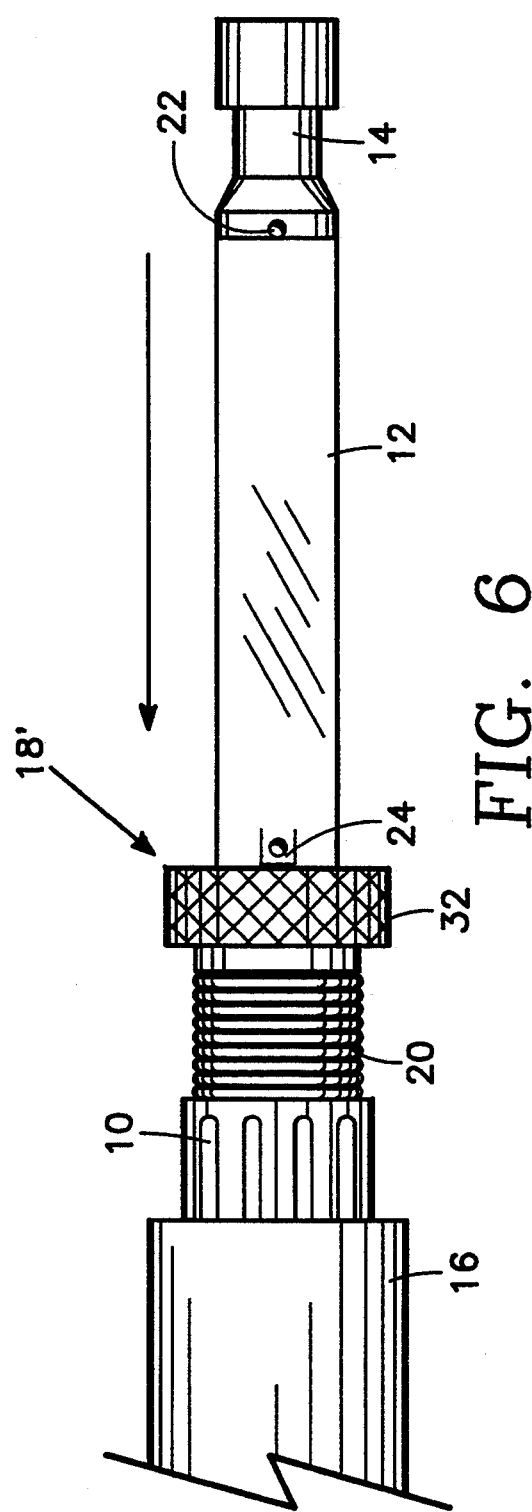

SPRINGS AND LOCKING COLLARS FOR RETRACTABLE SLEEVE-PROTECTED INJECTION APPARATUS

This application is a division of application Ser. No. 07/850,442, filed Mar. 10, 1992, U.S. Pat. No. 5,261,894.

BACKGROUND OF THE INVENTION

This invention relates to medical devices for injecting living bodies and, more particularly, to safety features incorporated therewith. In particular, it is directed to the springs and locking collars that can be used to releasably lock and automatically re-lock a retractable sleeve protecting the needle of a medical device.

In U.S. Pat. No. 4,998,922 by Thomas C. Kuracina entitled SAFETY SYRINGE CAP MINIMIZING NEEDLE-STICK PROBABILITY which issued 12 March 1991, a safety device for hypodermic needles and the like is shown. The inventions shown hereinafter are improvements thereto by inventors including and/or working with Mr. Kuracina. In the interest of simplicity herein, the teachings of that patent are incorporated herein by reference and the discussion of the background art will be kept to a minimum.

A typical prior art hypodermic syringe includes a barrel having a moving plunger therein. A needle having a sharp beveled tip extends from the end opposite the end of the barrel into which the plunger is inserted. The needle is covered by a removeable cap for safety purposes. The problem to be solved and avoided is the accidental sticking of users of the syringe by the tip after use where the tip may carry body fluids containing agents of hepatitis B, AIDS, and the like. Accidental needle stick is a very common problem in the health care industry and besides the risk of serious illness or even death as a result thereof, the insurance industry spends over a billion dollars a year in the testing of individuals who have been subjected to post-use needle stick.

The 1979 patent of Alvarez proposed a retractable plastic protective sleeve over the needle. The Alvarez sleeve has an inner hub which fits around the base of the needle and an outer hub through which the tip of the needle passes. The inner and outer hubs are connected by curved slats. When the needle is to be inserted into the body of a patient, the force required to move the sleeve from its extended position to its retracted position can be depicted as a straight line beginning with very little required force to initiate movement. Thus, there is really no actually safety from a large variety of ways in which accidental needle stick takes place. Even if the sleeve fully extends after use, a slight blow against a user or observer in the area will cause the sleeve to retract and the tip to stick the unfortunate person.

With respect to the action of the basic protective sleeve of the above-referenced Kuracina patent by comparison, a high degree of force is required to move the protective sleeve from its extended position covering the tip. Moreover, a spring-biased locking collar is added over the protective sleeve which all but prevents the protective sleeve from moving from its extended position covering the tip. The collar must be moved from its locked position to a retracted, unlocked position before the unique deformation qualities of the sleeve take effect. After use, the locking collar springs back to its locked position. Thus, in virtually all "accidental" contact with the tip end of a hypodermic syringe, actual penetration by the tip should be prevented.

In a co-pending application entitled MEDICAL INJECTION DEVICES WITH SAFETY FEATURES filed on even date herewith, certain improvements to the Kuracina protective sleeve are disclosed. The inventions described hereinafter are improvements to the spring and locking collar intended to make the Kuracina protective sleeve even safer and more easy to use while also adapting it to various mounting configurations.

Other objects and benefits of the inventions disclosed herein will become apparent from the detailed description which follows hereinafter when taken in conjunction with the drawing figures which accompany it.

SUMMARY

The foregoing object has been achieved in a protective sleeve for the needle of a medical device comprising a plurality of longitudinal slats extending from a base carrying a bottom end of the needle to an end-cap slidably mounted on the needle adjacent a tip end thereof when the protective sleeve is in an extended position and including a spring and locking collar disposed over the plurality of longitudinal slats with the spring between the base and the longitudinal collar, by the following inventions.

1. A unitary plastic helical compression spring comprising a cylindrical collar portion disposed over a center portion of the plurality of longitudinal slats with first and second portions of helical compression spring turns extending therefrom toward the base and the locking collar, respectively.

2. A unitary plastic helical compression spring capable of injection molding from a single point of injection comprising:
   a cylindrical collar portion disposed in a center portion of the spring and including a point of molding plastic injection;
   a first compression portion comprising a first plurality of helical compression spring turns extending longitudinally from the cylindrical collar portion in a first direction; and,
   a second compression portion comprising a second plurality of helical compression spring turns extending longitudinally from the cylindrical collar portion in a second direction.

3. An improved locking collar comprising a substantially cylindrical locking collar having an outside diameter larger than the outside diameter of the spring and of a thickness sufficient to produce a grippable area at the periphery thereof. Preferably, the grippable area at the periphery of the locking collar has a textured outer gripping surface for improving gripability thereof under adverse conditions.

DESCRIPTION OF THE DRAWINGS

FIG. 1 is a simplified, side view drawing of the Kuracina protective sleeve and spring-biased locking collar employing a plastic spring attached to a hypodermic syringe.

FIG. 2 is a simplified, side view drawing of the Kuracina protective sleeve and spring-biased locking collar employing a metal spring attached to a hypodermic syringe.

FIG. 3 is a simplified, side view drawing of the Kuracina protective sleeve and spring-biased locking collar employing an improved plastic spring according to this invention.

FIG. 4 is a partially cutaway view through the apparatus of FIG. 3.

FIG. 5 is a simplified, side view drawing of the Kuracina protective sleeve and spring-biased locking collar employing a metal spring and an improved locking collar shown in their extended position.

FIG. 6 is a simplified, side view drawing of the Kuracina protective sleeve and spring-biased locking collar employing a metal spring and an improved locking collar of FIG. 5 shown in their retracted position.

DESCRIPTION OF THE PREFERRED EMBODIMENTS

As described in the above-referenced Kuracina patent and with reference to FIGS. 1 and 2, the basic Kuracina protective sleeve comprises a hub 10 carrying a plurality of slats 12 terminating in an end piece 14. The hub 10 is fit over the base of a needle carried by the syringe 16. The needle passes between the slats 12 and passes through a bore (not shown) in the end piece 14. As the end piece 14 is retracted in use (either manually or by pressure against the skin of a patient), the slats 12 move outward as indicated by the ghosted positions and the needle tip is exposed. For added security, a slidable locking collar 18 is disposed over the slats 12 and biased towards the end piece 14 by a spring 20. In its extended position as shown in the drawing figures, the spring 20 prevents the outward flexing of the slats 12 and, thereby, the inward movement of the locking collar 18 to expose the tip of the needle. The locking collar 18 is prevented from coming off the end of the slats 12 and the end piece 14 by the front projection 22. Similarly, there is a rear projection 24 which holds the locking collar in its retracted position. When the slats 12 are flexed in use, the rear projection 24 is also flexed which releases the spring 20 and locking collar 18 to automatically re-lock the protective sleeve as the needle is withdrawn. Springs 20 of both plastic and metal as depicted in FIGS. 1 and 2, respectively, have been tested.

The use of plastic throughout is preferred as opposed to employing metal for the helical compression spring 20. A plastic spring, on the other hand, poses certain problems under the circumstances. The plastic is, of necessity, of a thicker diameter than metal providing the same spring quality. As a result, there are fewer turns in the spring 20 and the spacing between the turns is wider. It is possible, therefore, for the slats 12 to move between adjacent turns at the center of the spring 20 and allow the locking collar 18 and end piece 14 to move backward in combination thereby exposing the tip of the needle sufficient for accidental needle stick to occur. As a secondary consideration, reliably forming a plastic spring of the necessary length in an injection molding process by injecting from one end is questionable. Also, injection from both ends is impractical as the point of joining in the middle may be subject to breakage from a lack of proper merging of the plastic in its liquid form. The chances of a high reject rate due to improper forming of the spring is high in either case.

To eliminate both the foregoing problems, the spring 20' of FIGS. 3 and 4 is employed. The spring 20' includes a secondary collar 26 formed in the center thereof at the point of possible first contact by the slats 12 as they attempt to flex. Thus, the spacing between adjacent turns is eliminated in the area of concern and there is no chance that the tip 28 of the needle 30 will be exposed. Moreover, by injecting the plastic into the collar portion of the mold and having it flow bi-directionally into the portion of the mold defining the turns 27 of the compression spring portions 29, 29' on either side of the collar 26, the distance the liquid plastic has to flow to properly form the turns 27 is reduced to less than one-half and the chances of poorly formed springs 20' being produced is reduced to almost nil.

Another preferred improvement is shown in FIGS. 5 and 6. In this case, the generally cylindrical locking collar 18' is formed oversized; that is, of an enlarged thickness to form a grippable area at the periphery thereof and having an outside diameter larger than the outside diameter of the spring 20 so that the spring 20 is not contacted by a user's fingers when the locking collar 18' is gripped and retracted in combination with the spring 20. This provides for a surer grip when moving the locking collar 18' to its retracted position, which may have to take place under poor conditions such as with blood and/or other slippery bodily fluids covering the hands of the doctor or nurse employing the syringe 16. The oversized locking collar 18' may also be provided with a textured outer gripping surface 32 at the periphery thereof to improve its gripability under adverse conditions.

Wherefore, having thus described the present invention, what is claimed is:

1. A unitary plastic helical compression spring capable of being injection molded from a single point of injection comprising:
   a) an integral plastic cylindrical collar portion disposed in a center portion of the spring and including a point of molding plastic injection;
   b) an integral plastic first compression portion comprising a first plurality of helical compression spring turns extending longitudinally from said cylindrical collar portion in a first direction; and,
   c) an integral plastic second compression portion comprising a second plurality of helical compression spring turns extending longitudinally from said cylindrical collar portion in a second direction.

2. A unitary plastic helical compression spring prepared by a process comprising the steps of:
   injection molding from a single point of injection located at a center portion of the spring such that liquid plastic flows bi-directionally from the single point of injection to form a structure comprising,
   an integral cylindrical collar portion disposed in a center portion of the spring,
   an integral first compression portion comprising a first plurality of helical compression spring turns extending longitudinally from said cylindrical collar portion in a first direction, and,
   an integral second compression portion comprising a second plurality of helical compression spring turns extending longitudinally from said cylindrical collar portion in a second direction.

* * * * *